(12) United States Patent
Koj

(10) Patent No.: US 10,334,376 B2
(45) Date of Patent: Jun. 25, 2019

(54) HEARING SYSTEM WITH USER-SPECIFIC PROGRAMMING

(71) Applicant: KOJ Institut fuer Gehoertherapie AG, Zurich (CH)

(72) Inventor: Andreas Thomas Koj, Zurich (CH)

(73) Assignee: KOJ Institut für Gehoertherapie AG, Zürich (CH)

( * ) Notice: Subject to any disclaimer, the term of this patent is extended or adjusted under 35 U.S.C. 154(b) by 13 days.

(21) Appl. No.: 15/386,689

(22) Filed: Dec. 21, 2016

(65) Prior Publication Data

US 2017/0105079 A1 Apr. 13, 2017

Related U.S. Application Data

(63) Continuation of application No. PCT/EP2015/065527, filed on Jul. 7, 2015.

(30) Foreign Application Priority Data

Jul. 9, 2014 (CH) ........................................ 1047/14

(51) Int. Cl.
*A61B 5/12* (2006.01)
*H04R 25/00* (2006.01)

(52) U.S. Cl.
CPC ............ *H04R 25/70* (2013.01); *A61B 5/121* (2013.01); *A61B 5/123* (2013.01); *H04R 25/558* (2013.01);
(Continued)

(58) Field of Classification Search
CPC .. H04R 25/70; H04R 25/558; H04R 2225/43; H04R 2225/55; A61B 5/121; A61B 5/123
(Continued)

(56) References Cited

U.S. PATENT DOCUMENTS

| 2004/0049125 A1 | 3/2004 | Nakamura et al. |
| 2006/0235332 A1 | 10/2006 | Smoorenburg et al. |

(Continued)

FOREIGN PATENT DOCUMENTS

| DE | 102004025691 B3 | 8/2005 |
| EP | 2200347 A2 | 6/2010 |

(Continued)

OTHER PUBLICATIONS

International Search Report for PCT Application No. PCT/EP2015/065527, dated Sep. 25, 2015, 11 pages.
(Continued)

*Primary Examiner* — Sean H Nguyen
(74) *Attorney, Agent, or Firm* — Brake Hughes Bellermann LLP

(57) ABSTRACT

Systems and methods pertaining to a hearing system programming device are described. The hearing system programming device includes a test signal generator configured to generate at least one acoustic test signal, at least one acoustic reproduction unit or a transmission unit for transmitting the at least one test signal to a reproduction unit, an input unit designed to receive a response of a user in reaction to the at least one test signal, a program modification unit designed for determination of a modified programming of a hearing system while taking into consideration the received reaction, a trainable configuration storage unit, and a communication unit designed for a data communication with the hearing system and for a transmission of the modified programming to the hearing system. A hearing system arrangement including a hearing system programming device and a method for programming a hearing system in a patient-specific manner are also described.

20 Claims, 6 Drawing Sheets

(52) U.S. Cl.
CPC ...... *H04R 2225/43* (2013.01); *H04R 2225/55* (2013.01)

(58) Field of Classification Search
USPC .......................................................... 381/314
See application file for complete search history.

(56) References Cited

U.S. PATENT DOCUMENTS

| | | | |
|---|---|---|---|
| 2010/0202625 A1* | 8/2010 | Boretzki | H04R 25/70 381/60 |
| 2010/0329490 A1 | 12/2010 | Van Schijndel et al. | |
| 2011/0219879 A1* | 9/2011 | Chalupper | A61B 5/12 73/585 |
| 2011/0249839 A1 | 10/2011 | Mindlin et al. | |
| 2013/0085411 A1 | 4/2013 | Van Tasell et al. | |
| 2013/0121496 A1* | 5/2013 | Boretzki | H04R 25/70 381/60 |
| 2013/0202124 A1 | 8/2013 | Bellanova et al. | |
| 2015/0358745 A1* | 12/2015 | Rix | H04R 25/305 381/60 |

FOREIGN PATENT DOCUMENTS

| | | |
|---|---|---|
| WO | 2005125281 A1 | 12/2005 |
| WO | 2010091480 A1 | 8/2010 |
| WO | 2015009561 A1 | 1/2015 |

OTHER PUBLICATIONS

Swiss Search Report for Application No. CH 01047/14, dated Mar. 10, 2015, 4 pages.
Examination Report issued in EP Application No. 15 736 240.1 dated Jan. 30, 2019 along with statement of relevance, 10 pages.

* cited by examiner

HEARING SYSTEM WITH USER-SPECIFIC PROGRAMMING

CROSS REFERENCE TO RELATED APPLICATION

This application claims priority to and is a continuation of, PCT Application No. PCT/EP2015/065527, filed on Jul. 7, 2015, entitled "HEARING SYSTEM WITH USER-SPECIFIC PROGRAMMING", which, in turn, claims the benefit of priority based on CH Application No. 01047/14, filed on Jul. 9, 2014, both of which are hereby incorporated by reference.

TECHNICAL FIELD

This disclosure pertains to the area of the hearing systems, and in particular pertains to hearing aids and implantable hearing systems and their programming.

BACKGROUND

Hearing systems for the improvement of hearing ability have been used for many years in great numbers and in principle are well known. Typical designs include various forms of behind-the-ear devices and in-the-ear devices, but also other specialized systems, such as bone conduction hearing aids and implantable systems, or in particular, implantable hearing aids and cochlear implants.

Hearing systems corresponding to the current state of the art frequently have complex digital signal processing and are programmable in numerous parameters, for example via remote control devices, special programming devices and/or PCs.

SUMMARY

In one general aspect, a method for the user-specific programming of a hearing system is described. The method may include providing a hearing system programming device for the hearing system and executing at least one data collection sequence. Executing the at least one data collection sequence may include generating and emitting at least one acoustic test signal, and receiving at least one response of a user of the hearing system in reaction to the at least one test signal by the hearing system programming device, the response coding hearing comprehension of the user in relation to the at least one test signal. The method may also include executing at least one programming sequence, the at least one programming sequence including, determining a degree of hearing comprehension for the received response, determining a modified programming of the hearing system as a function of the determined degree of hearing comprehension by the hearing system programming device. The determination of the modified programming may take into account an evaluation of the received at least one response of the user of the hearing system. The method may also include transmitting the modified programming of the hearing system programming device to the hearing system over a data communication link established between the hearing system programming device and the hearing system and modifying the programming of the hearing system to the modified programming.

In another general aspect, a hearing system programming device is described. The hearing system programming device may include a test signal generator configured to generate at least one acoustic test signal. The device may further include at least one acoustic reproduction unit operatively coupled to the test signal generator and designed for the acoustic emission of the at least one test signal, and a transmission unit operatively coupled to the test signal generator for the transmission of the at least one test signal to a reproduction unit. The device may also include an input unit designed for the reception of a response of a user in reaction to the at least one test signal, the response coding the hearing comprehension of the user in relation to the at least one test signal. The device may also include a program modification unit designed for the determination of a modified programming of a hearing system and further designed to determine the modified programming taking into consideration a degree of hearing comprehension determined for the received response. The device may also include a trainable configuration storage unit which is operatively coupled to the program modification unit for storing a configuration of the programming of the hearing system. The device may also include a communication unit designed for a data communication with the hearing system and for a transmission of the modified programming to the hearing system.

The details of one or more implementations are set forth in the accompanying drawings and the description below. Other features will be apparent from the description and drawings, and from the claims.

DETAILED DESCRIPTION

Figure 1:
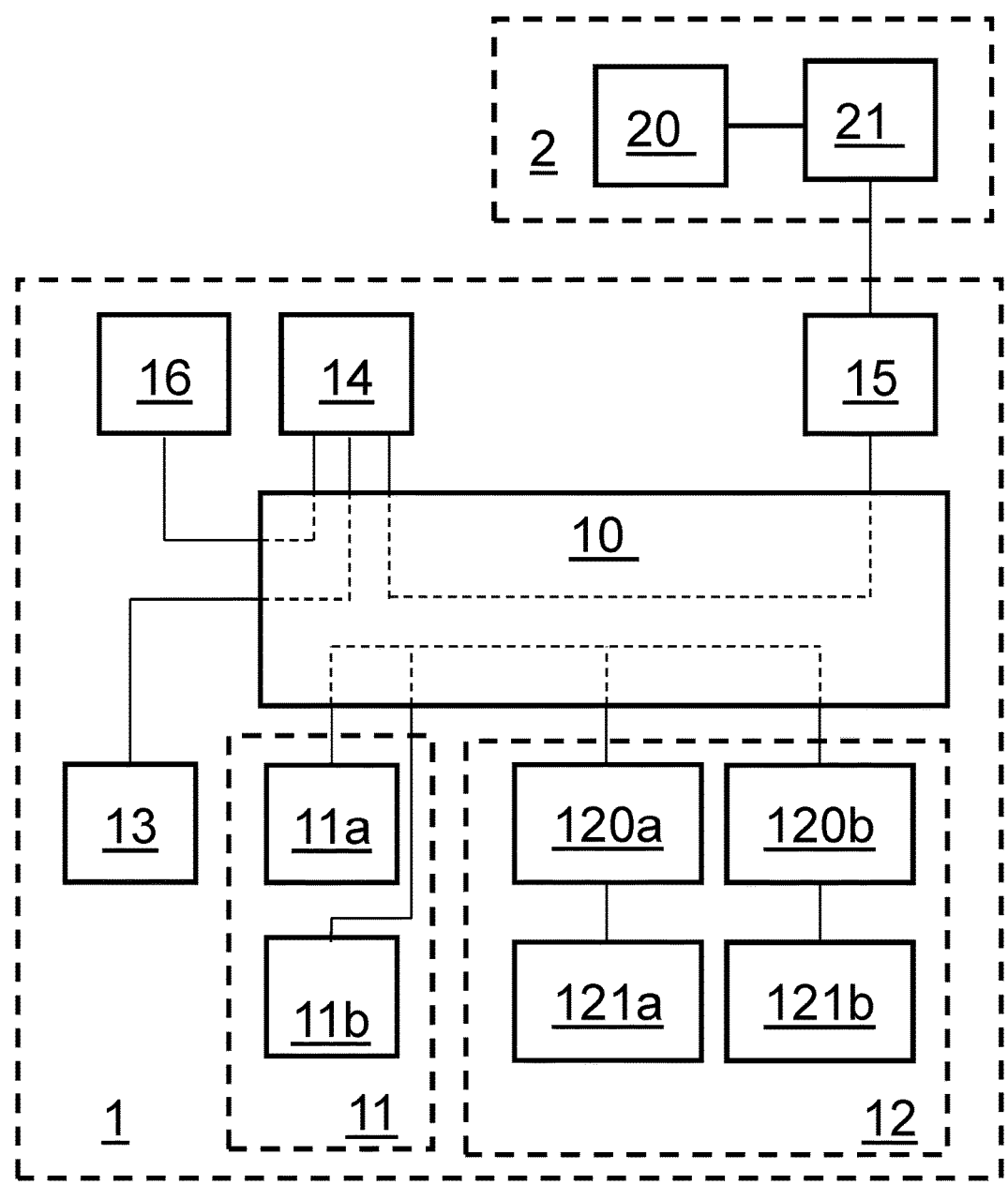
FIG. 1 shows an exemplary hearing system arrangement having a hearing system and a hearing system programming device in a schematic structural and functional view.

Notwithstanding the technical progress in the area of hearing systems and their elaborate and sophisticated design, the improvement in hearing ability achieved in everyday use by a hearing system in many cases can be unsatisfactory for users of such systems. The use of the hearing system can be discontinued based on such dissatisfaction. Frequently, a substantial reason for this is that the subjective hearing capability is not improved or only slightly improved in everyday situations despite the amplification realized by the hearing system, while the subjective perception of noise and disturbing sounds is increased because of the amplification by the hearing system. The options for counteracting these problems by means of the hearing system design and, in particular, the (digital) signal processing are limited and generally unsatisfactory according to the present state of the art.

While a hearing system, for example, a hearing aid of known design, operates on a purely acoustic and physical level and increases the sound pressure impinging on the eardrum, subsequent processing in the brain is of central importance for (speech) comprehension and other perception processes associated with hearing (e.g., direction, location) and this has been broadly learned. In principle, the brain of a person having healthy and undamaged hearing capability in interaction with an undamaged sense of hearing is capable in particular of concentrating on certain sound events of interest (e.g., a voice that is whispering or superimposed by intense disturbing sounds) and blocking out or masking other sound events and sound signals.

However, with incipient and progressive hearing loss, the brain extensively loses this ability for acoustic "concentration;" the ability to distinguish useful (e.g., valid, recognizable) acoustic signals of interest from other noise signals get lost. The subsequent use of a hearing system, for example a hearing aid, in many cases, essentially results in subjective perception of more noise, but not a satisfactory improvement of hearing capability.

This disclosure describes a way to improve the situation in the use of hearing systems. This objective is achieved by a method for patient-specific programming of a hearing system, a hearing system programming device, and a hearing system arrangement as well as a computer program product directed to the same. Specific advantageous embodiments are described throughout this disclosure and accompanying figures.

In general, the disclosure may describe at least one method for the user-specific programming of a hearing system. The method may include providing a hearing system programming device for the hearing system and executing at least one data collection sequence. Executing the at least one data collection sequence may include generating and emitting at least one acoustic test signal, and receiving at least one response of a user of the hearing system in reaction to the at least one test signal by the hearing system programming device, the response coding hearing comprehension of the user in relation to the at least one test signal. The method may also include executing at least one programming sequence, the at least one programming sequence including, determining a degree of hearing comprehension for the received response, determining a modified programming of the hearing system as a function of the determined degree of hearing comprehension by the hearing system programming device. The determination of the modified programming may take into account an evaluation of the received at least one response of the user of the hearing system. The method may also include transmitting the modified programming of the hearing system programming device to the hearing system over a data communication link established between the hearing system programming device and the hearing system and modifying the programming of the hearing system to the modified programming. The at least one acoustic test signal is generated by the hearing system programming device. The emission can likewise be done by the hearing system programming device. However, in other embodiments, the at least one acoustic test signal can also be emitted by other external reproduction units. Such a reproduction unit can in particular be formed by the programming hearing system itself, as explained further below. In embodiments of this type, the method includes a transmission of the at least one test signal from the hearing system programming device to the external reproduction unit.

The hearing system can in principle be of any known design and in particular a behind-the-ear or in-the-ear device. However, it can also be a bone conduction hearing aid or an implantable system, in particular an implantable hearing aid or a cochlear implant. The hearing system can further include two essentially separate devices, each of which is assigned to an ear of the user.

The user or wearer of the hearing system is referred to in this document as "user," This user is frequently a person with limited hearing capability or with partial hearing loss. However, the user can also be a person with another ailment that impairs hearing ability, for example a tinnitus, an oversensitivity, a lack of concentration and/or other deficits in auditory processing, for example, an attention deficit disorder (ADD), an attention deficit/hyperactivity disorder (ADHD) or an auditory processing disorder (APD). In yet other implementations, the user may not have an ailment or hearing impairment and may instead utilize the methods and systems described herein to determine hearing ability and measure a degree of understanding in response to hearing test sounds.

As described further below in connection with exemplary embodiments, the at least one test signal in conjunction with the assessment of the user's response provides a data basis for the modification of the hearing system programming. In addition, the test signal can serve in several embodiments as a training signal, which can be used to train the user's brain with regard to his/her capability to correctly evaluate and classify sound events and in particular to distinguish between useful (e.g., predefined signal, recognizable signal, valid signal, etc.) signals and noise signals. A method for patient-specific programming of a hearing system is provided in which the programming is adaptively adjusted to the hearing capability and hearing comprehension of the user. As presented below, this adaptation can be done over a longer time frame in a continuous or distributed manner, changes in hearing capability occurring within this time frame being taken into account in the programming of the hearing system.

The "programming" of the hearing system includes the totality of all adjustable or selectable parameters for the patient-specific adaptation of the hearing system, such as global (frequency-unspecific) amplifications, frequency-dependent or frequency-specific amplifications, additional filters or compression parameters of a dynamic compression in the hearing system, parameters of limiters as well as other functions provided in some hearing systems, such as a microphone selection.

The programming can additionally or alternatively relate to other or additional programmable parameters, depending on the specific situation.

In some embodiments, the evaluation of the at least one response of the hearing system user includes a comparison of the at least one response to a corresponding reference response. The determination of programming modification is therefore based at least partially on the result of the comparison. The reference answers can, for example, be queried online from an external database or be stored in a memory of the hearing system programming device, for example, in the form of a database.

As described in detail further below, the reference response may correspond to the correct resolution of an (acoustic) exercise or generally to the correct recognition of an acoustic situation, and other alternative responses to an incorrect resolution of an exercise or the incorrect one of an acoustic situation. In this context, the response of the user can be understood as an answer to a question determined by the test signal. The response of the user is accordingly classified in a binary manner either as "correct" or "incorrect." In this case incorrect responses in particular, that is, ones that do not correspond to the reference responses, indicate a need for a change in the programming, for example, of the amplification. By contrast, a correct response or a correct answer indicates that there is no requirement for modification of the programming for the hearing system with respect to the acoustic aspect covered by the particular exercise.

In practice, instead of a comparison of an individual response to an individual reference response, a number of responses can be compared to a corresponding number of reference responses and be taken into consideration for the determination of the modified programming, each emission of a test signal and the reception of an associated response corresponding to the resolution of an individual exercise by the user. A modification of the programming can occur, for example, if—for a series of identical or similar exercises or test signals—the portion of incorrect answers (responses that do not correspond to the respective reference response) exceeds a threshold. As illustrated in detail further below, the individual exercises may also be completed in a time-distributed manner, for example, over a period that may extend from days to weeks.

The procedure proposed here, in contrast to approaches known in the art, has the advantage that a modification in the programming of the hearing system is done on the basis of objective and verifiable criteria, and not primarily on the basis of subjective assessment of the programming by the user. Due to the fact that the reference responses (and, thus, the correct answers to the exercises) are present in the hearing system programming device and the comparison is made by the hearing system programming device, it also is not required for the user to recognize the test signal beforehand. Instead of this—corresponding to situations typically occurring in everyday life—he/she is confronted with sound events that are unknown to him/her in the specific configuration. The solutions known in the art relate to the fact that the same test signal with different programming of the hearing system is presented to the user, and he/she subjectively decides about the best variant. In some embodiments, the at least one test signal includes at least one random component. A random component can be realized, for example, via a random number generator and relate, for example, to one or more of the following aspects: Selection of a test signal; composition of the test signal from a useful signal (e.g., predefined signal, recognizable signal, valid signal, etc.) and a noise signal as described below; volume of the test signal; voice from spoken components of the test signal; direction from which the test signal comes; frequency or pitch of the test signal; musical instrument with which a note sequence or melody is played; duration of the presentation or emission of the test signal.

In some embodiments, the at least one test signal includes a distorted test signal, the distorted test signal comprising a useful signal (e.g., predefined signal, recognizable signal, valid signal, etc.) and a noise signal. In some embodiments with a distorted test signal, the noise signal includes a constant noise signal and/or at least one pulse signal. The noise signals can be synthesized by the hearing system programming device—realized, for example, by a hardware and/or software noise generator—as well as by stored real disturbing sounds, with which a user is typically confronted in everyday life.

In some embodiments with a distorted test signal, the method includes an increase and/or lowering of a level of the noise signal relative to the useful signal (e.g., predefined signal, recognizable signal, valid signal, etc.) as a function of the received at least one response of the hearing system user. In particular, a response given by the user may alternatively correspond to a correct or incorrect resolution of a predetermined exercise. Then, an increase in the level of the noise signal can occur in the case of a high proportion of correct answers, whereupon the user is gradually accustomed to acoustically difficult situations without being overwhelmed. When there is a low number of correct answers, the level of the noise signal can be reduced accordingly or a further increase in the noise signal level can be omitted or at least slowed. The harmonization of the ratio between noise signal and useful signal (e.g., predefined signal, recognizable signal, valid signal, etc.) can be done uniformly for all exercises and test signals or separately and adaptively for different types of exercises and test signals. Therefore, for acoustic situations in which the user (still) makes relatively few mistakes, a lower noise level can generally be selected, for example, than for exercises and test signals in which the user has answered mostly or completely correctly, that is, the response corresponds to the respective reference response.

In some embodiments, the at least one test signal includes at least one of the following: spoken digits, numbers, sounds, syllables, phonemes, words, word groups, sentences, notes, rings and note sequences or melodies. In principle, a test signal or a useful signal (e.g., predefined signal, recognizable signal, valid signal, etc.) can include as a component of the test signal such acoustic signals as are perceived and to be processed by the user of the hearing system in everyday life, in particular speech and its components.

In some embodiments, the method includes the execution of a number of data collection sequences, wherein the particular at least one generated test signal differs, between the individual data collection sequences, for at least a portion of the data collection sequences.

In some embodiments, having a number of data collection sequences, the method includes the execution of a number of data collection sequences over a number of days, in particular over a number of successive days. Each day, one or in turn a sequence of data collection sequences can be carried out. Furthermore, the steps of the evaluation of the user response or responses, the determination of a modified programming of the hearing system and the modification of the programming of the hearing system can be carried out multiple times a day on each of the days or only on a portion of the days.

In some embodiments, the determination of the modified programming of the hearing system includes a determination of a modified amplification. The amplification is considered here as a function of the frequency and so is generally different for different frequencies.

In some embodiments with a change of the amplification, the determination of the modified amplification includes the determination of a frequency-dependent change of the amplification as a function of the at least one response of the user. A "frequency-dependent change of the amplification" may be used to indicate that the targeted selective change of the amplification for one or a number of specific frequencies or frequency ranges, while the amplification remains unchanged for the remaining frequencies or frequency ranges. The determination of the modified amplification can in particular be done as a function of and in consideration of the at least one response by the user. As illustrated in detail further below in connection with exemplary embodiments, an embodiment of this type allows in particular a targeted harmonization of the hearing system programming to the effect that sound events that are similarly sounding—and thus critical in their differentiation, in particular consonants and in generally phonemes—can be differentiated at least well enough by the user.

In some embodiments with a change of the amplification, the determination of the changed amplification includes the determination of a frequency-independent change of the amplification as a function of the at least one response of the user. A "frequency-independent change of the amplification" is a change in the amplification that relates generally to the acoustic range process-able by the hearing system and essentially in the same way, for example an increase in the amplification by a pre-determined number of decibels over the entire frequency range. A frequency-independent change of the amplification can include—based on responses of the user to test signals as previously described, but also independently thereof—occurring on a time-controlled basis, for example.

In some embodiments of this type, the method includes the execution of a number of programming sequences with a step-by-step increase of the amplification in the direction of a target amplification. When the method is executed distributed over a time frame of several days, as previously described, individual steps of the step-by-step increase in the amplification, in particular the frequency-independent amplification, may occur on different days. As explained in connection with exemplary embodiments, the method can also include a reduction or a lowering of the amplification and/or a retention of the amplification without modification. In the case of an execution of the method distributed over a time frame of several days, the previous amplification may, for example, remain unchanged or be lowered on some days.

In some embodiments of this type, the method includes the execution of a first program step and the subsequent execution of a second program step. The first and second program steps each include the execution of at least one data collection sequence. The determination of the modified amplification is done in the first programming step in a frequency-independent programming stage. In the second programming stage, the determination of the modified amplification is frequency dependent In some embodiments of this type, the execution of each of the first and second programming steps is done distributed over several days.

A hearing system programming device may include a test signal generator configured to generate at least one acoustic test signal. The device may further include at least one acoustic reproduction unit operatively coupled to the test signal generator and designed for the acoustic emission of the at least one test signal, and a transmission unit operatively coupled to the test signal generator for the transmission of the at least one test signal to a reproduction unit. The device may also include an input unit designed for the reception of a response of a user in reaction to the at least one test signal, the response coding the hearing comprehension of the user in relation to the at least one test signal. The device may also include a program modification unit designed for the determination of a modified programming of a hearing system and further designed to determine the modified programming taking into consideration a degree of hearing comprehension determined for the received response. The device may also include a trainable configuration storage unit which is operatively coupled to the program modification unit for storing a configuration of the programming of the hearing system. The device may also include a communication unit designed for a data communication with the hearing system and for a transmission of the modified programming to the hearing system.

The hearing system programming device can be designed for the execution of a method for the application-specific programming of a hearing system. A hearing system programming device is this provided that permits a patient-specific programming of a hearing system in such a way that the programming adapts to the changing hearing ability of the user.

In one embodiment, the program modification unit is designed to carry out a comparison of the at least one response to a corresponding reference response and to determine the modified programming at least partially based on the result of the comparison. Other features and variants further result directly from the disclosure of methods.

The aforementioned functional components of the hearing system can be structurally realized in a single device or distributed in different devices.

Thus, described embodiments and variants of the method for user-specific programming of a hearing system likewise disclose corresponding embodiments of a hearing system programming device. In an analogous way, embodiments of the hearing system programming device likewise disclose corresponding embodiments of the method for the programming of a hearing system.

A hearing system arrangement may include a hearing system programming device as described above and below and a programmable hearing system. The hearing system has a communication interface designed for a data communication with the communication unit and for changing its programming by means of data received via the communication interface of the hearing system.

Just like a hearing aid programming device described herein, a hearing system arrangement can be realized in a structurally distributed manner. FIG. 1 shows a hearing system arrangement in a schematically structural and functional view. The hearing system arrangement includes hearing system programming device 1 and hearing system 2. Hearing system 2 is assumed by way of example to be an external hearing aid, for example a behind-the-ear device or in-the-ear device of generically known design, but may also be another type of hearing system corresponding to the general description. Furthermore, hearing system 2 can be formed by two separate device, for example, two external hearing aids of the previously described type, each of which is assigned to an ear of the user.

The basic functionality of hearing system 2 is illustrated in consolidated form in a functional unit 20. This unit 20 is operatively coupled to bi-directional communication interface 21.

Hearing system programming device 1 includes a central control unit 10, a test signal generator 11, an acoustic reproduction unit 12, an input and display unit 13, a program modification unit 14, a trainable configuration memory 16, a bidirectional communication unit 15, which is designed for a data communication with communication unit 21 of hearing system 2.

Central control unit 10 represents the central command module of hearing system programming device 1. Central control unit 10 controls and coordinates the sequence of the steps and functions carried out by hearing system programming device 1. The remaining functional components of hearing system programming device 1 are operatively coupled to central control unit 10. In embodiments described in detail below, in which a method for user-specific programming of hearing system 2 is implemented in a time-distributed manner, wherein, with the method for executing the method being organized according to exercises, tasks and lessons to be completed by the user, central control unit 10 controls in particular the sequence of the exercises, tasks and lessons and, thus, the overall sequence of the method.

Test signal generator 11 includes a useful signal generator 11a and a noise signal generator 11b. Test signal generator 11 provides the test signals with their respective useful signals and noise signals. Useful signals as well as noise signals can be provided by useful signal generator 11a or noise signal generator 11b in the form of acoustic signals that are recorded and saved in digital form, for example in the form of speech, background noise, etc. recorded according to known methods of sound recording technology. The use of recordings of "genuine" acoustic signals has the advantage of an especially natural sound that, in the example of speech, is identical to a real human voice. However, useful signal generator 11a and/or noise signal generator 11b of test signal generator 11 may, alternatively or additionally, also be designed for the synthesis of artificial test signals or parts of test signals. For this purpose, useful signal generator 11a may, for example, include an arrangement for speech synthesis, and noise signal generator 11b [may include] pulse generators and noise generators of a generally known type.

Acoustic reproduction unit 12 has, for example, two channels and is thus designed for the acoustic reproduction and emission of stereo signals. Acoustic reproduction unit 12 respectively includes an amplifier 120a or 120b and a speaker 121a or 121b for each channel, the left and the right. Amplifiers 120a, 120b and speakers 121a, 121b are designed in a fundamentally known manner and may, as needed, also have a number of paths for different frequencies, plus frequency filters. Acoustic reproduction unit 12 further includes (not separately illustrated in FIG. 1) digital-to-analog converters for the conversion of the test signals provided in digital form.

In alternative embodiments, the hearing system programming device does not include an acoustic reproduction unit 12. Instead, test signals are reproduced via a transmission unit, which can be formed by the communications interface 15 explained in detail further below and/or by another interface, transmitted directly to the hearing system 2 and reproduced by it.

Input and display unit 13 is assumed here to be, for example, a touchscreen. However, it can also additionally or alternatively include other devices, such as a mouse, a conventional keyboard, an audio-response unit with microphone, a camera-assisted apparatus for the detection and evaluation of hand movements and/or gestures and/or facial features, etc.

Communication unit 15 for bidirectional data communication with communication unit 21 of hearing system 2 is designed in a generally known way, for example according to the Bluetooth standard or as an NFC unit (near field communication unit). However, it can also include a WLAN module, an infrared interface or a galvanic interface with electrical contacts.

Functional components and the working principle of program modification unit 14 as well as trainable configuration memory 16 is explained in detail below in reference to the operation of the hearing system arrangement.

The illustration according to FIG. 1 primarily provides an overview of the interaction of the individual functional components of the hearing system arrangement. It implies no special limiting technical realization. Therefore, functional components separately depicted in FIG. 1 can be fully or partially integrated in a specific technical implementation. Likewise, an individual functional component can be realized via a number of structural components. Furthermore, the realization of hearing system programming device 1 is typically accomplished with a mixture of hardware components as well as software and/or firmware components that are stored in a non-volatile memory. A central component of hearing system programming unit 1 in typical embodiments is a computer unit with generally known components accordingly programmed via software and/or firmware. They can provide additional components, such as the touchscreen as input and display unit 13, and by appropriate programming realize in particular central control unit 10 and program modification unit 14 as well as trainable configuration memory 16. Of course, other designs are also possible in which most or all functional components are formed by appropriately specialized hardware. The corresponding connections and signal paths between individual functional units or components of hearing aid programming device 1 in FIG. 1 illustrate exemplary operative connections between the respective connections or components in the shown exemplary embodiment without excluding additional connections or alternative realizations.

In the embodiment depicted in FIG. 1, the hearing system arrangement is structurally and functionally self-contained and can function with other external equipment, devices or system components, such as external computers, databases or servers.

In other also possible embodiments, the hearing system programming device is realized in a distributed manner its functionality, wherein individual functional components are realized, for example, in the form of an external unit, the, for example, external server and/or databases. A local unit then typically includes communications interface 21, acoustic reproduction unit 12 and the input and display unit 13. Other components can be wholly or partially located in the external unit. The external and local units thus communicate via corresponding generally known communication interfaces and communication channels, such as an Internet connection. An architecture of this type makes it possible in particular to locate data- and/or computing-intensive functions wholly or in part to the external unit. As a result, the local unit can be designed in a comparatively compact, technically less complex and economical manner. The external unit can include, for example, databases or libraries of test signals that are transmitted as needed wholly or in part to the local unit. Likewise, the external unit can provide functionalities for the modification of the programming of hearing system 2, as in the form of modification algorithms stored as program code, lists and look-up tables.

Likewise, an overall sequence made up of tasks, exercises and lessons, as previously described and described below in reference to examples, can be permanently stored in a memory of the central control unit 10 or transmitted wholly or in part from an external unit.

Figure 2:
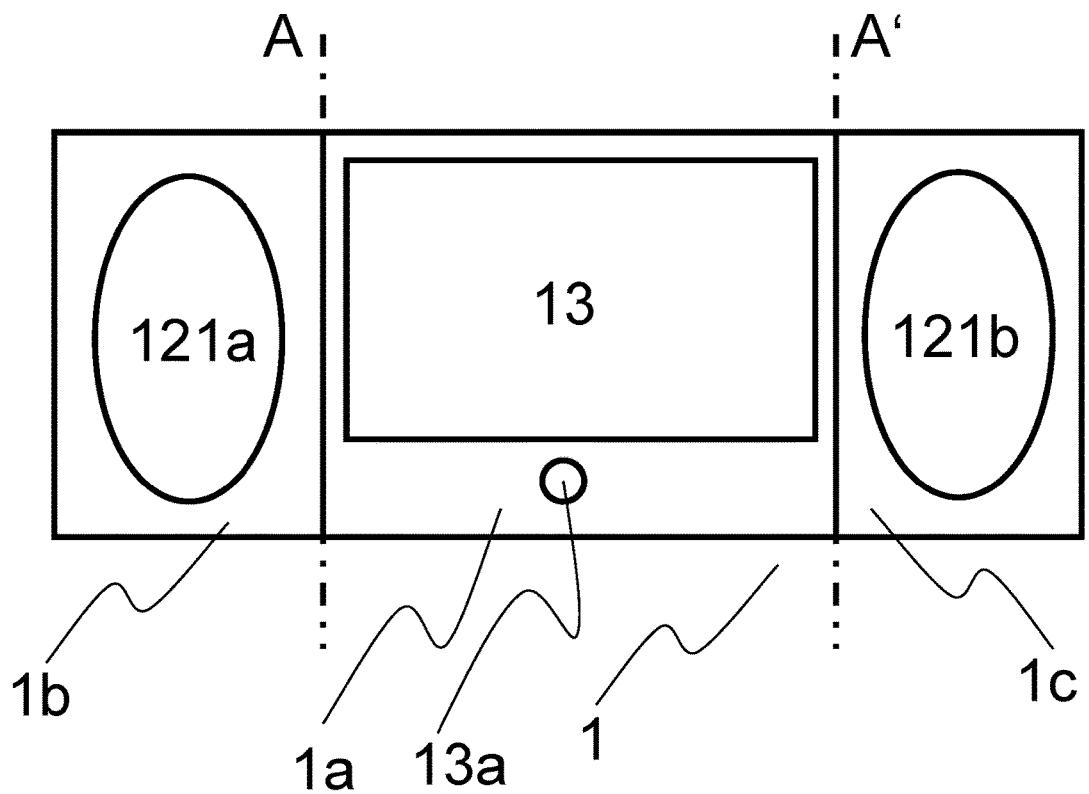
FIG. 2 shows an exemplary outer design of a hearing system programming device in schematic view.

Reference is additionally made below to FIG. 2. FIG. 2 shows a possible outer configuration of a hearing system programming device 1 according to FIG. 1 in schematic view. The components of hearing system programming device 1 are divided over three modules 1a, 1b, 1c, each with its own module housing. Hearing system programming device 1 is designed for use in the arrangement on a table or the like, the view shown if FIG. 2 being tilted in relation to the table surface in the manner of a lectern.

Module 1a is a centrally arranged main module that typically holds most of the components of hearing system programming device 1 and in a typical embodiment holds in particular the computer. The two side modules 1b, 1c arranged to the left and right, respectively, of main module 1 hold the two speakers 121a, 121b in particular but may also hold other components, e.g., amplifiers 120a, 120b connected upstream of the speakers. The distance between speakers 121a, 121b is to be set in such a way that there is a good stereo location for a typical operating distance of, for example, 30 cm to 50 cm. FIG. 2 shows hearing system programming device 1 in its operational state. In the interest of compact dimensions during storage and transport, side modules 1b, 1c are mounted on (not separately referenced) hinges on main module 1a so that it can be folded along hinge line A, A' on the main module for transport and storage. In the closed state, side modules 1b, 1c are held in their closed position, for which permanent magnets situated on the inside may be advantageously present.

Input and display unit 13, designed as a touchscreen, occupies a majority of the surface of main module 1a. In addition to the function as an input unit, touchscreen 13, where applicable in connection with speakers 121a, 121b, is used as a general user interface for the operation of hearing system programming device 1. In addition to touchscreen 13, hearing system programming device 1 may have other controls. In FIG. 2, a master switch 13a is shown.

Figure 3:
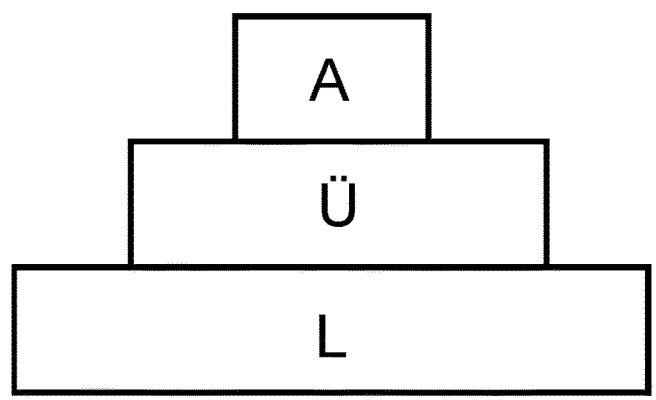
FIG. 3 schematically shows a possible configuration of the sequence of a method for patient-specific programming of a hearing system.

Reference is additionally made below to FIG. 3. FIG. 3 schematically shows a hierarchical approach for an exemplary execution of a method for user-specific programming of a hearing system.

The illustrations below assume that a hearing system 2 for carrying out a method is configured or programmed for a specific user. For this purpose—in a generally known way—audiological tests are carried out, for example by a hearing aid acoustician and/or doctor and in this way the individual hearing deficits are established from which the individual method procedure is determined. For the configuration for an individual user, hearing system programming device 2 can store a number of modules with tasks, exercises and lessons, which are selected in an initial phase and combined into an individual sequence. The execution of the method controlled and coordinated by central control unit 10 is then done on the basis of this individual programming or configuration. Alternatively, the individual configurations can also be called up or transmitted as previously described.

The execution of the method is accompanied by the completion of a series of lessons L by the user, the individual lessons L being completed in a time interval. The steps associated with one and the same lesson L are carried out essentially directly in succession and in one unit.

Each section L includes a series of exercises Ü to be completed in succession. Each exercise Ü addresses a specific set of subjects that is to be taken into account in the user-specific programming.

Each exercise Ü includes a series of tasks A. A task A includes the presentation of at least one sound event in the form of the emission of at least one test signal by the hearing system programming device 1 to which the user reacts by input of a response corresponding to a task that is prescribed and, for example, communicated via touchscreen 13. Depending on the exercise, an exercise may include, in addition to an acoustic test signal, also other components, in particular, for example, information visually displayed on touchscreen 13, for example, a picture that falls within a context of meaning with the acoustic test signal.

An exercise Ü is made up of a sequence of essentially identical tasks A in a different specific manifestation, as presented further below. Each completed task A can be alternatively classified as "correctly resolved" or "incorrectly resolved" based on the response given by the user, or a degree or a percentage portion for which the particular task was correctly resolved can be determined. The same applies for exercises Ü and lessons L as higher level units. The exercise is correctly resolved if the response obtained by the user corresponds to the reference response.

The contents of the individual tasks A, exercises U and lessons L are formed in such a way that the particular test signals used in connection with the evaluation of the responses of the user form a database for the user-specific modification of the programming of hearing system 2. Furthermore, they are used for training the user in the manner described above, whereupon hearing system programming unit 1 is likewise used as a hearing training device. The sequence illustrated here with the structure according to tasks, exercises and lessons represents just one example of a possible structure of the time sequence of the method.

Figure 4:
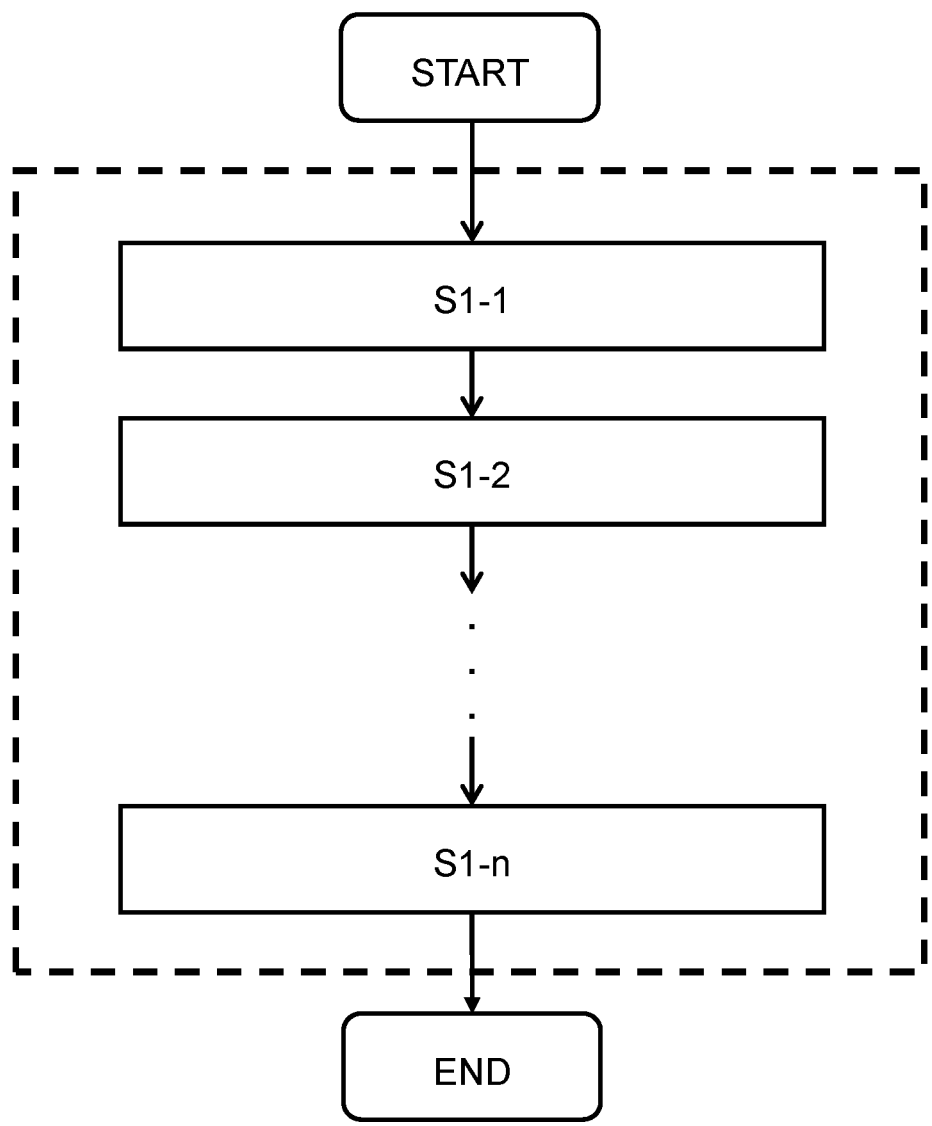
FIG. 4 schematically shows the sequence of a method for patient-specific programming of a hearing system.

Reference is additionally made below to FIG. 4. FIG. 4 shows an exemplary sequence of a method for the user-specific programming of hearing system 2 via hearing system programming device 1 in the form of a simplified flow diagram.

The user-specific programming corresponding to the present disclosure is accomplished in steps S1-1 to S1-$n$, each of which runs in essentially the same way and each of which includes a lesson L. The user-specific programming is carried out in time over n days—for example, successive days—on each day x, a corresponding step S1-$x$ being carried out. The execution of step S-1-$x$ is accompanied by the completion of a corresponding lesson L-x. The overall duration of the method may, for example, be 20 or 30 days, corresponding to n=20 or n=30, respectively. The duration for the execution of each step S1-$x$ and, thus, the duration for the completion of a lesson by the user is, for example, approximately 45 minutes. The individual lessons are designed to build upon each other and possess a complexity and difficulty the progresses over time, as described in detail further below. Therefore, each of steps S1-1 to S1-$m$ is generally designed the same, as described below.

Figure 5:
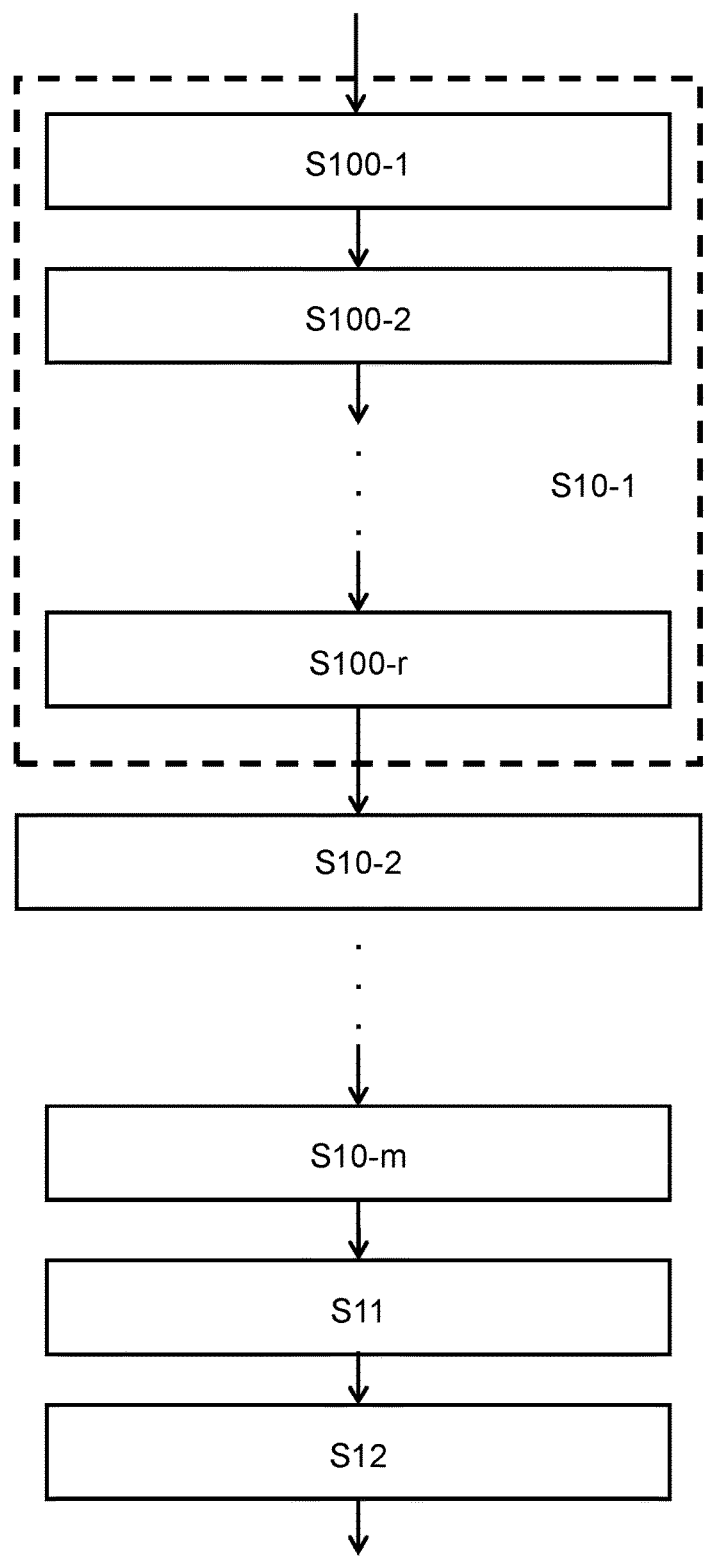
FIG. 5 shows in a schematic way the sequence of a method for patient-specific programming of a hearing system according to FIG. 4.

Reference is additionally made below to FIG. 5. FIG. 5 shows an exemplary sequence for an individual step S1-$x$ according to FIG. 4 in the form of a simplified flow diagram.

The lesson L-x assigned to step S1-$x$ includes the completion of a series of exercises to which the sequential steps S10-1 to S10-$m$ are assigned, where m represents the number of exercises in a lesson. The number m of exercises in this context may be the same or different for the various lessons L-x. Typically, m is, for example, in a range from three to eight.

Each exercise includes the completion of a series of exercises to which the successive method steps S100-$x$-1 to S100-$x$-$r$ are assigned. In this, each of steps S10-1 to S10-$m$ is basically designed in such a way as is depicted in FIG. 5 for step S-10-1, for example. The number r of the tasks may be the same or different for the individual exercises.

Optionally, after the completion of each task or, where applicable, exercise, an indication is given to the user of whether and the extent to which the task/exercise was resolved. This can be done, for example, by textual and/or symbolic and/or color indications on touchscreen 13. Furthermore, the optional possibility of repeating an "incorrectly" resolved task can be provided, wherein the total number of repetitions may be limited to a number of, for example, three.

After the completion of last exercise m, an evaluation is performed in step S11-$x$ in which programming modification unit 14 and/or the central control unit 10 carries out an evaluation of the responses received in the individual exercises and tasks via touchscreen 13. Based on this evaluation, a modified programming for hearing system 2 is determined by program modification unit 14 and stored in the trainable configuration memory 16, as described below.

comprehension; dichotic hearing; linking of acoustic and visual perception; associative hearing. The following table indicates exemplary exercise types for different disciplines.

TABLE 1

Exemplary Exercise Types

| Discipline | Task(s)/exercise(s) |
|---|---|
| Speech comprehension | Comprehension of double-digit and triple-digit or generally x-digit numerical words; Comprehension of individual words of different numbers of syllables, in particular "similar" sounding words (for example, Dinkel, Dunkel, Winkel [similar sounding German words]); Comprehension of individual syllables; Comprehension of sets and flowing text; Comprehension both forward and in modified sequence (e.g., reverse) of reproduced numerical words, numerical sequences or word sequences. |
| Dichotic hearing | Comprehension of the content reproduced from one channel (e. g. a spoken sentence), while a different content (another spoken sentence) is simultaneously reproduced over the other channel. |
| Linking of acoustic and visual perception | Assignment of a heard acoustic stimulus or an acoustic perception (e.g., of an expression; sentence, tone, sound, a melody) to one of a number of images depicted on the touchscreen (visual stimulus; optical perception) |
| Associative hearing | Counting the frequency of numbers, words or characteristic tones (e.g., clanging of glass) in a longer heard passage. |

While the determination of the modified programming is depicted as separate step S11 in FIG. 5, the execution of step S11 can also be done in a time-distributed manner, for example, in each case directly following the conclusion of an exercise and, thus, in each case within steps S10-1, S10-2 . . . S10-$m$. Likewise, it can be done continuously during the completion of the tasks and/or exercises.

In the next step S12, a transmission of the modified programming determined in step S12 is done via communication unit 15 of hearing system programming unit 1 and communication unit 21 of hearing system 2, and a change is made in the programming of hearing system 2 from the initial programming present at the beginning of step S1-$x$ to a programming modified in relation thereto. This modified programming in turn forms the initial programming for the next lesson x+1 and with it the next step S1-[x+1]. Alternatively, just as previously described for step S11, the possibility also exists of changing the programming and with it to carry out step S12 in a time-distributed manner.

Trainable configuration memory 16 stores the programming of hearing system 2, which changes during the application of the method, and thus represents an adaptive memory for the programming of hearing system 2 corresponding to the modification of the programming of hearing system 2.

In other alternative variants, step S12, and where applicable also step S11, is not carried out within each step S1-$x$ and, thus, within the context of completing each lesson, but instead only within a part of these steps, for example within the context of every second, third or fifth step S1-$x$.

In the exemplary embodiment described here, the smallest, and thus elementary form of a data collection sequence is done through each task A. Each task A is oriented toward an aspect or a number of specific aspects of the hearing and the acoustic perception that a person typically masters for the perception and processing of acoustic signals, and the mastery thereof by a user equipped with a hearing aid is the determining factor for the benefits achieved in everyday life by using the hearing aid. Some examples of aspects of this type (also called "disciplines") are (for example): Speech For the individual tasks/exercises, the user interface of the hearing system programming device is used in each case, e.g., touchscreen 13, which in each case provides a graphical user interface corresponding to the exercise, e.g., an alphanumeric keyboard, check boxes, spin wheels, etc.

For a portion of the disciplines with the particular associated tasks/exercises, for example speech comprehension, a test signal that is identical in each case is emitted via the two reproduction channels of hearing system programming device 1. In other disciplines, in particular dichotic hearing and stereo location, the test signals are instead different for the left and right channels.

The contents to be understood by the user (words, syllables, numbers, sentences, etc.) each represent a useful signal (e.g., predefined signal, recognizable signal, valid signal, etc.). A noise signal can be superimposed on the useful signal (e.g., predefined signal, recognizable signal, valid signal, etc.). The noise signal in this case is an essentially uniform noise signal and/or a brief pulse signal. Examples of uniform noise signals are generally traffic noise, the typical background noise of a restaurant or open-plan office, the rushing of a stream, crashing waves, etc. Examples for pulsed noise signals are a church bell and a short dog bark or telephone ringing.

Central control unit 10 controls the composition of the test signals from useful signal and noise signal in such a way that over time the noise portion or noise level becomes greater, that is, the signal-to-noise ratio (SNR) decreases. In the case of the exemplary classification of the method according to FIG. 4, the noise level can, for example, increase with each of steps S1-$x$ or only with every second or third step. When there is an increase in the noise level between each step S1-$x$ and the subsequent step S1-[x+1] the signal-to-noise ratio drops accordingly from step to step. In the case of the exemplary execution of a step S1-$x$ per day, the signal-to-noise ratio accordingly becomes somewhat less from day to day. As a function of the responses given by the user via input unit (13), the noise level can, however, also remain the same or even be reduced via central control unit (10) for different days, as explained in detail further below.

In addition to a basic increase in the noise level over time, as described, central control unit 10 further controls the noise level as a function of the responses received from the user during the completion of the individual tasks/exercises. In the process, the portion of the particular exercises that were correctly resolved by the user is assessed in particular. The better the exercises and tasks have been resolved by the user, the larger the portion of the responses corresponding to a correct answer (in other words, the larger the portion of the responses corresponding to the particular reference response), the more sharply the noise level is increased or the signal-to-noise ratio reduced. In this way, increasingly difficult tasks/exercises are presented to the user during the application of the method, but the user also is not overwhelmed under the particular concrete circumstances. The control of the noise level described here as a function of the user's responses is advantageous in particular under the aspect of auditory training, but with regard to the modification of the hearing system programming is not compulsory.

The time-controlled increase in the noise level can, for example, be done consistently between each of the individual steps S1-x, the signal-to-noise ratio being lowered, for example, by the same level each time. Because, blocking out pulse-type noise signals for the user is more difficult than blocking out essentially continuous signals, it can further be provided to provide pulse-type noise signals only in a continued state of applying the method or, depending on the specific situation, to completely refrain from doing so.

If the portion of responses that correspond to a particular correct answer is low, the noise level can also be left unchanged or even reduced. For this purpose, central control unit 10 can compare the number or the portion of correctly resolved tasks in each case to adjustable or fixed threshold values and adapt the noise level as a function of the comparison. Therefore, a lower and an upper threshold can be saved for the number or the portion of correct answers. If this falls below the lower threshold, the central control unit reduces the noise level; if it exceeds the upper threshold, it [the central control unit] reduces it [the noise level] accordingly. If the number or the portion of correct answers is between the threshold values, the noise level remains unchanged. Corresponding threshold values may be identical for all exercises or different for at least some exercises.

For special cases, such as advanced hearing loss, in users or patients with other relevant diseases, such as Alzheimer's disease, etc., it is also possible to omit the noise signal completely or partially so that the test signals include just a useful signal. Such an omission can likewise be displayed in the course of the improvement of the distinguishability of similar sounding tones, as described in detail further below.

The selection of the useful signal in the individual exercises can be done randomly in some cases. Thus, for example, numbers, words, syllables and sentences can be selected by central control unit 10 and/or test signal generator 11, in particular useful signal generator 11a, via a random generator from an extensive collection of numbers, letters, words, sentences, etc. which are stored in test signal generator 11. In a similar way, the selection of noise signals can be made wholly or in part on a random basis.

The execution of the method in the previously described manner in, for example, daily lessons occur in such a way that the basic complexity and difficulty of the particular tasks, just like the noise level according to the above illustration, increases over time. Other complications can be achieved, for example, by measures such as an increase in the speaking speed and/or a switch between different speakers with different voices and/or different volumes.

As previously mentioned, a modification of the programming of hearing system 2 occurs in each of steps S11, S12. For more detailed explanation of this aspect, reference is also made below to FIG. 6, which in an initial aspect shows in particular a frequency-independent modified amplification in a first aspect of a change in the programming of hearing system 2 by hearing system programming device 1 in steps S11, S12.

Figure 6:
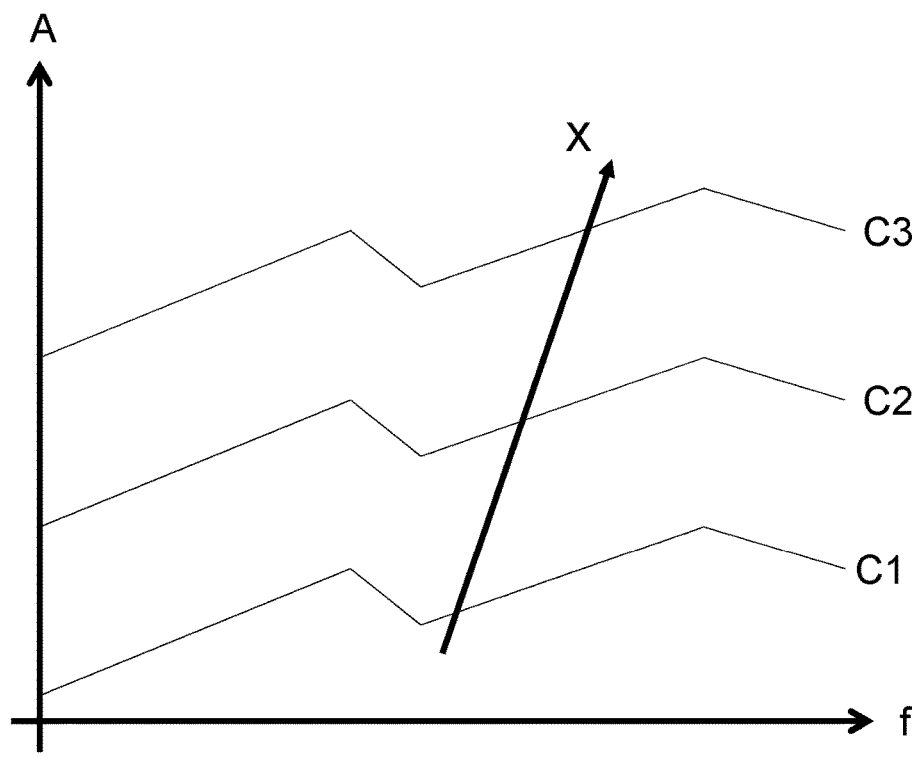
FIG. 6 schematically shows a frequency-independent change of the amplification of the hearing system over time.

Hearing system 2 has an amplification A, which is programmable as a function of frequency f and which is generally known in the art. Amplification A can be depicted in a diagram as a curve that is a function of the frequency. FIG. 6 shows as an example three curves C1, C2, C3 assumed to be linear, the ordinates of the diagram logarithmically corresponding to the depiction of the level. The qualitative course of the curves corresponds here to the (frequency-dependent) amplification, which may compensate for the loss of hearing ability that exists when hearing system 2 is not used.

For an ideally complete compensation of the loss in hearing ability, it would be desirable in principle to set amplification A in such a way that the volume perceived by the damaged hearing with hearing system corresponds to the volume perceived by the undamaged hearing with hearing aid. However, in practice, this is hardly fully possible. This is due in particular to the fact that when a hearing loss exists, the brain quickly loses the ability to suppress disturbing sounds in the perception and thereby block out or mask them. A complete or at least extensive compensation for the hearing loss by a correspondingly high setting of the amplification would therefore lead to perception of disturbing noises that is subjectively sensed as unbearably loud and in some cases painful.

According to some embodiments described herein, the strengthening of the hearing system is distributed over a longer time frame and is expanded, for example, step by step. In this way, the hearing of the user is accustomed to higher amplifications over a longer time frame without the amplification increasing over time resulting in an unacceptable increase in the subjectively perceived volume of the disturbing noises. Accordingly, amplification A, as indicated by arrow X, increases over time from exemplary initial curve C1 through curve C2, as an exemplary intermediate distance, up to curve C3, as an exemplary end state on completion of the method, curve C3 representing the target amplification as a function of the frequency.

A frequency-independent change in the amplification of the previously represented type can be controlled over time and independent of the responses received from the user in reaction to the test signals. Optionally, however, responses of the user can be taken into consideration. These responses are typically not answers to tasks of the previously illustrated type and typically do not underlie the previously illustrated binary classification based on the comparison to a reference response. Responses of this type relate instead to the well-being and the listening comfort of the user. Thus, in particular when a method is carried out over a longer time frame of several weeks at different points in time, for example, within the context of each step of the step-by-step increase in the amplification, it can be provided that the user indicates in each case whether the current amplification is pleasant for him/her, bordering on too loud or too loud (unbearably loud). Depending on the response, the method can extend the provided time up until the end state (curve C3) is reached, reduce the amplification sought in the target state or else—in the event of an acutely excessive amplification—reduce the current amplification. Furthermore, it can be provided that the user himself/herself triggers the instant of the next step of an increase of the amplification in the direction of the sought end state via an entry.

Alternatively or in addition to the change of the hearing system programming via a generally frequency-independent (unspecific) change in the amplification as previously described, the method can include a selective change in the amplification at specific frequencies or within specific frequency ranges. With this measure, the ability to differentiate with respect to similar sounding letters, syllables or phonemes (here collectively referred to as "sounds") can be improved in a targeted manner.

Figure 7:
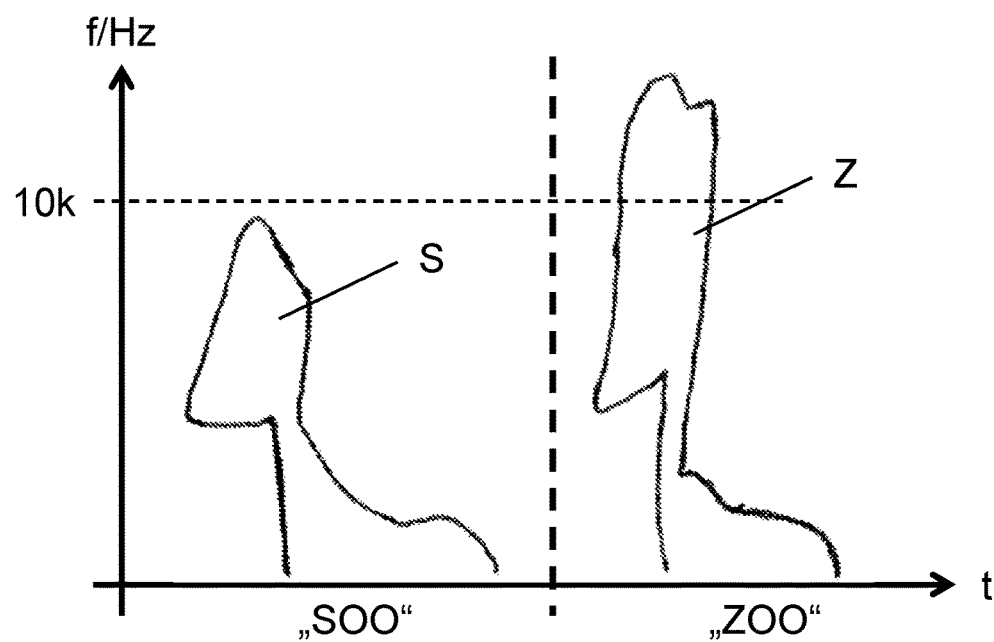
FIG. 7 schematically shows the contours of spectrograms for two exemplary similar sounds.

Reference is additionally made below to FIG. 7. FIG. 7 shows as an example and in a schematic way in a common diagram the important contours of the spectrograms for a spoken "SOO" [German pronunciation] (left) or a spoken "ZOO" [German pronunciation] (right). It is obvious that the spectrograms differ in particular within a frequency range above 6 kHz. This frequency range is clearly present for "ZOO," for "SOO" on the other hand it is not.

For a user who cannot or can only insufficiently differentiate the sounds corresponding to the spoken "S" [German pronunciation] and "Z" [German pronunciation] individually and/or in words, the programming of the hearing system 2 changes in such a way that the amplification is selectively raised within this differentiating frequency range. In this way the perceived difference increases and with it the ability to differentiate between the sounds.

In the example of FIG. 7, the differentiation between "S" and "Z" is made over a single narrow frequency range. However, the differentiation in the case of other sounds or sound pairs can also be made over two or more frequencies or frequency ranges that occur either just within the spectrum of one of the sounds or else are present within the spectra of the two sounds but with substantially different amplitude or power level. Frequencies and frequency ranges of this type, which can be employed for the differentiation of similar sounding sounds, are shown here in summary form as differentiating frequency ranges.

Useful signals with difficult to differentiate sounds, such as spoken letters, syllables, words and/or phonemes are stored in useful signal generator 11a of test signal generator 11 for this purpose. In these embodiments, the corresponding spectral components can be stored in program modification unit 14 in, for example, the form spectrograms according to FIG. 7 that are stored in tables. Alternatively or additionally, the differentiating frequencies or frequency range can also be directly stored for pairs and/or groups of sounds. The spectrograms of individually spoken sounds are extensively invariant in the course of their quality with respect to the person speaking, so that they or values derived from them can be stored in general form. Design of the spectrograms for different sounds and methods for their determination are generally known within the technical field of auditory acoustics.

A sequence of exemplary method steps for the frequency-dependent change of the programming according to the previously illustrated approach is illustrated below with additional reference to FIG. 8. Data on the ability to differentiate between difficult to differentiate sounds are gathered in a data collection sequence having steps S10a-1 to S10a-m. The individual exercises with steps S10a-x are carried out in this context in the previously described way. It is assumed here that just the ability to differentiate between two sounds, such as "S" and "Z," is ascertained and is to be improved if necessary. For different sounds or sound groups, the method as described here can be performed sequentially. However, in principle it is also possible to carry out the method simultaneously with respect to a series of sounds or sound pairs and then to modify the programming of hearing system 2 in a common step. Furthermore, it is assumed in the illustration of FIG. 8 that the data collection is done in the form of a series of different exercises to which steps S10a-1 to S10a-q are assigned and each of the exercises includes a sequence of tasks. The individual tasks may, for example, be separately oriented toward the distinguishability of individual letters, syllables and words. Of course, it is also possible, however, to provide just one exercise having an appropriate number of similar tasks.

Following the tasks/exercises, an evaluation is done in step S11a in the previously described manner. As a result, the extent to which and in which proportion the tasks/exercises have been correctly resolved by the user. In the next step S13a, a determination is made of whether the user's differentiation ability is satisfactory or sufficient. This can, for example, be done by comparing the portion of tasks/exercises that was resolved correctly to a threshold value. In the positive case, no modification of the programming of hearing system 2 is required, and the method is continued with other tasks, exercises or lessons. In the negative case, the determination of a modified programming of hearing system 2 is done by the program modification unit in step S12a and a corresponding change of the programming. For this reason, as previously described in reference to FIG. 7, the amplification is selectively modified for a differentiating frequency range or a number of differentiating frequency ranges. In addition to a frequency-selective increase, a frequency selective reduction of the amplification is also possible here.

Following the modification of the programming of hearing system 2, the execution of a new data collection sequence and a corresponding evaluation as well as the assessment with regard to satisfactory or sufficient ability to differentiate are accomplished. In this way it is possible to establish whether the targeted improvement of the ability to differentiate has been achieved. If this is not the case, step S12a is executed again and with it the amplification is further modified.

In principle, step S12a and with it the frequency-dependent modification of the amplification can be carried out multiple times in succession. Actually, limits are set on increasing the amplification by noise signals also being accordingly amplified in the frequency range related to differentiation. Therefore, the increase in the amplification in step S12a can be limited for security reasons to a prescribed maximum value.

In step S12a, the amplification can in each case be changed, e.g., increased, by a fixed amount. Alternatively, the change may, however, also be carried out as a function of the preceding evaluation in step S13a. If, say, the user exhibits a substantial deficit with regard to differentiation of two sounds (characterized by a low portion of correct resolutions of the tasks/exercises), a relatively large change in the amplification of one or more specific frequency ranges can occur in step S12a. If a deficit with regard to the differentiation of the sounds is present but small, a lesser change in the amplification can instead occur in step S12a.

In data collection steps S10a-1 to S10a-q, the useful signals in an exemplary embodiment is at first not superimposed with a noise signal. Following the change in the programming that occurs in some cases, the level of the noise signal can be increased in subsequent steps (not explicitly depicted in FIG. 8). Likewise, it is also possible to directly carry out a superimposition of useful sound and disturbing sound or to provide test signals having different noise levels in the data collection sequence having steps S10a-1 to S10a-q.

Other examples of sounds or sound groups occurring in everyday life in which the differentiation of different consonants is frequently critical and their differentiation capability can accordingly be approved by an amplification change in selected frequency ranges: "AZA—ADA—AGA—ATA—ASA—ABA—AFA—AKA—ALA—ANA—APA—ACHA—AWA" or "IFI—IZI—ISI—IGI".

In contrast to the previously illustrated example of the sounds "SOO" and "ZOO," the two examples just cited are not limited to exactly two alternatives, but instead relate to a greater number of sounds that in every case are similar sounding. The procedure here can follow the method sequence from FIG. 8, wherein in step S11a it is advantageously ascertained between which sounds there is sufficient ability to differentiate and the determination of the modified programming in step S12a relates to frequency ranges that are characteristic in each case for these sounds. Likewise, the method according to FIG. 8 can be separately and/or jointly carried out for different sound groups. When there is a joint execution, test signals from different sound pairs or pair groups can, for example, be presented to the user in randomized sequence.

Figure 8:
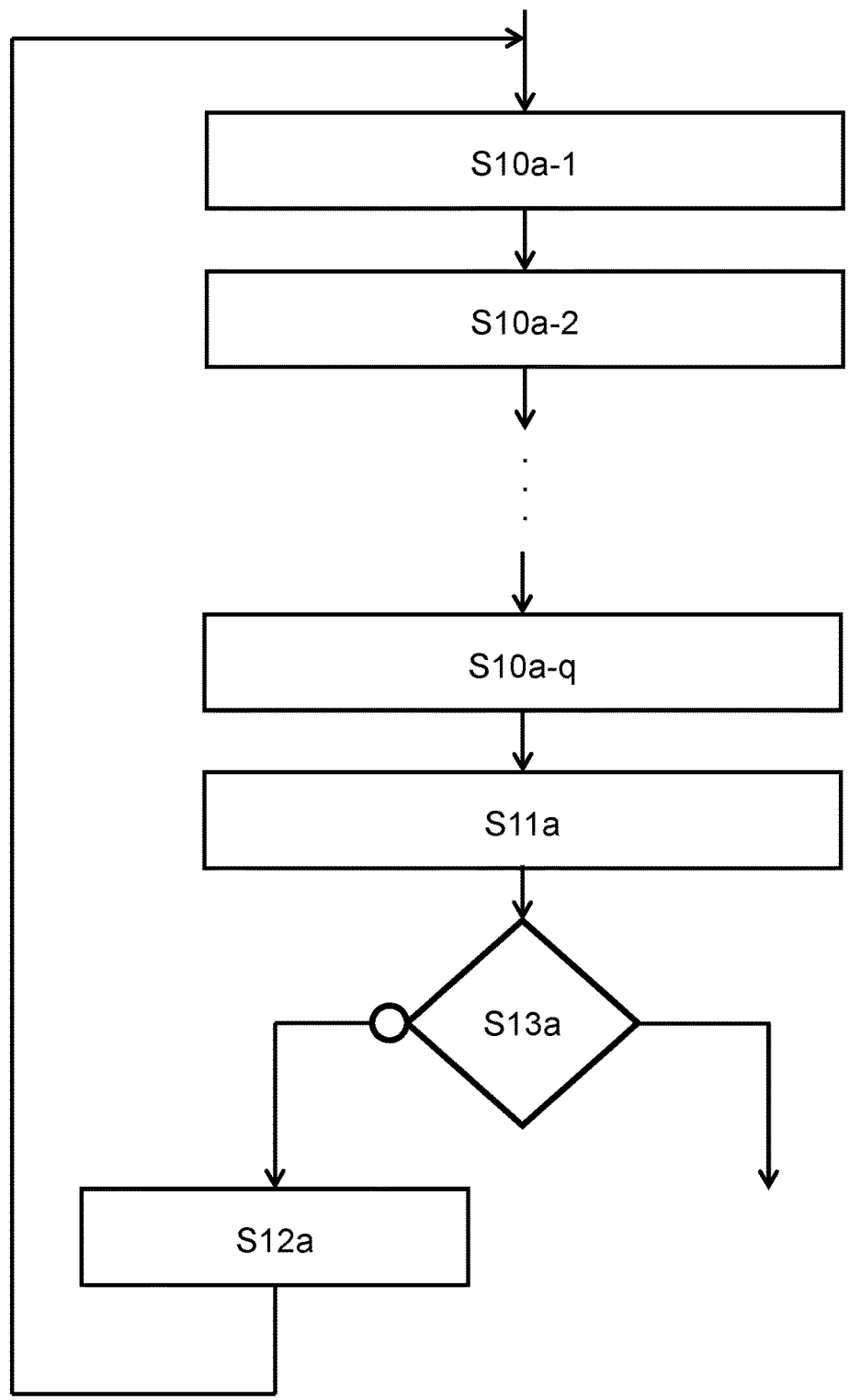
FIG. 8 schematically shows the sequence of a frequency-dependent change of the amplification of the hearing system.

In a further example for a frequency-dependent change in the amplification according to FIG. 8, the test signals are not made up of spoken sounds, syllables or phonemes as previously presented, but of sounds, for example, of different and similar sounding musical instruments that are detectable by the user. The frequency-dependent change of the amplification then includes a change of the frequency range(s) that are characteristic for the different sound of the instruments (overtone spectrum).

In a further example for the modification of the amplification according to FIG. 8, the modification is done on a frequency-independent basis. This may make sense, for example, if the user exhibits a deficit with regard to the directional location or the stereo location. In this case, in steps S10a-1 . . . S10a-q test signals are emitted from different directions, for example, "left," "middle" and "right," where additional intermediate stages can also be provided. The response of the user exists in an indication of the heard direction of the perceived sound event. Through the evaluation in steps S11a/S13, a determination is then made of whether—if the extent the user uses a hearing aid for each ear—the amplification of one of the hearing aids in comparison to the other, which is expressed in a poor location capability in this direction. In this case, the amplification in step S12a is accordingly adjusted, for example, by increasing the amplification in one hearing system or reduction of the amplification in the other.

The data for a frequency-dependent and/or frequency-independent modification of the amplification can be stored in hearing system programming device 2, for example, in the form of lists or tables (look-up tables) in which, for example, the frequency ranges that are characteristically different for different phonemes or phoneme combinations (see FIG. 7 and associated illustration above) are stored. However, it is also possible that data of this type are wholly or partially stored in a central unit, as explained in connection with FIG. 1, and are called up by hearing system programming device 2 via, for example, an Internet-based communication interface, or transmitted to it.

Both a frequency-independent and a frequency-dependent change in the amplification can in principle by jointly carried out or be alternately carried out in a sequence. In a specific embodiment, however, the method according to FIG. 1 is carried out in two successive programming steps. In the first programming step, the amplification is thus changed on an exclusively frequency-dependent basis, in particular increased, as depicted in FIG. 6 and previously described. In the next two programming steps, the amplification is changed only selectively and on a frequency-dependent basis for the improvement of the differentiation capability corresponding to FIG. 7 and accompanying description. In an exemplary embodiment, the execution of the first programming step can extend, for example over a time frame of 20 days, and the second programming step over a subsequent time frame of another 10 days, where each of the phases can include a sequence of lessons, tasks and exercises according to the above illustration.

Just as described in relation to the frequency-independent modification of the amplification of hearing system 2, the modifications made in the programming of hearing system 2 are stored in trainable configuration memory 16.

In one variant it is further possible to provide the trainable configuration memory instead or additionally in hearing aid programming device 1 in hearing system 2. In embodiments of this type, a transmission of the programming from hearing system 2 to hearing aid programming device 1 or a comparison between the programming saved in hearing system 2 and hearing aid programming device 1 occurs in each case during or after the establishment of a communication link between the communication interfaces 15 and 21. In embodiments in which in the hearing system programming device, as shown in FIG. 1, the trainable configuration memory 16 is still present, the storage of a changed programming can first be locally stored in this configuration memory and be transmitted from this to hearing system 2. In embodiments in which a trainable configuration memory is only present in the hearing system, the memory of the changed programming can occur directly there.

Current hearing systems with digital signal processor corresponding to the prior art further make it possible to program the amplification differently as a function of the frequency (see FIG. 6) for different input volumes of the noises affecting the microphone(s) of the hearing system, that is, to amplify noises of varying loudness differently as a function of the frequency, a classification into, for example, four ranges of (input) volumes typically occurring. Likewise, hearing deficits can relate exclusively or primarily to specific volume ranges. Methods and hearing system programming devices can accordingly be configured in such a way that the previously described method are applied wholly or partially separately for different (input) volume ranges. In embodiments of this type, the emitted test signals possess different volumes and modifications in the programming of the hearing system; two occur in each case for the related (input) volume range. The execution of data collection sequences can, for example, be done jointly for the different (input) volume ranges, but the evaluation and modification of the programming can be done at least partially separately.

What is claimed is:

1. A method for user-specific programming of a hearing system, wherein the method comprises:
   providing a hearing system programming device for the hearing system;
   executing at least one data collection sequence, the at least one data collection sequence including, generating and emitting at least one acoustic test signal that includes at least one spoken element, and receiving at least one response of a user of the hearing system in reaction to the at least one test signal by the hearing system programming device, the response coding hearing comprehension of the user in relation to the at least one spoken element of the at least one test signal;

executing at least one programming sequence, the at least one programming sequence including, determining, by the hearing system programming device, a degree of hearing comprehension for the received response by comparing the received response to a corresponding reference response, the reference response being present in the hearing system programming device and corresponding to a correct resolution of an acoustic exercise represented by the test signal, determining a modified programming of the hearing system as a function of the determined degree of hearing comprehension by the hearing system programming device, the determination of the modified programming taking into account an evaluation of the received at least one response of the user of the hearing system;

transmitting the modified programming of the hearing system programming device to the hearing system over a data communication link established between the hearing system programming device and the hearing system; and modifying the programming of the hearing system to the modified programming.

2. The method according to claim 1, wherein the at least one test signal includes at least one random component.

3. The method according to claim 1, wherein the at least one test signal includes a distorted test signal, the distorted test signal including a predefined signal and a noise signal.

4. The method according to claim 3, wherein the noise signal includes a uniform noise signal and at least one pulse signal.

5. The method according to claim 3, wherein the method comprises an increase or decrease of a level of the noise signal relative to the predefined signal as a function of the received at least one response of the user of the hearing signal.

6. The method according to claim 1, wherein the at least one test signal comprises at least one of the following: spoken digits, numbers, sounds, syllables, phonemes, words, word groups, sentences, notes, sounds and note sequences, and melodies.

7. The method according to claim 1, wherein the method includes the execution of a plurality of data collection sequences, the at least one generated test signal differing from the individual data collection sequences, for at least a portion of the data collection sequences.

8. The method according to claim 7, wherein the method includes the execution of a number of data collection sequences over a plurality of days.

9. The method according to claim 1, wherein the determining the modified programming of the hearing system includes:

a determination of a modified amplification as a function of the at least one response of the user; and a determination of a differentiation ability of the user corresponding to the acoustic exercise represented by the test signal.

10. The method according to claim 9, wherein the determination of the modified amplification includes the determination of a frequency-dependent change of the amplification.

11. The method according to claim 9, wherein the method includes the execution of a plurality of programming sequences with a step-by-step increase of the amplification in the direction of a target amplification.

12. A hearing system programming device, the system comprising:

a test signal generator configured to generate at least one acoustic test signal;

at least one acoustic reproduction unit operatively coupled to the test signal generator and designed for acoustic emission of the at least one test signal that includes at least one spoken element, and a transmission unit operatively coupled to the test signal generator for the transmission of the at least one test signal to a reproduction unit;

an input unit designed for the reception of a response of a user in reaction to the at least one test signal, the response coding hearing comprehension of the user in relation to the at least one spoken element of the at least one test signal;

a program modification unit designed for the determination of a modified programming of a hearing system and further designed to determine the modified programming taking into consideration a degree of hearing comprehension determined for the received response by comparing the received response to a corresponding reference response, the reference response being present in the hearing system programming device and corresponding to a correct resolution of an acoustic exercise represented by the test signal;

a trainable configuration storage unit which is operatively coupled to the program modification unit for storing a configuration of the programming of the hearing system; and a communication unit designed for a data communication with the hearing system and for a transmission of the modified programming to the hearing system.

13. The system according to claim 12, wherein the at least one test signal includes a distorted test signal, the distorted test signal including a predefined signal and a noise signal.

14. The system according to claim 13, wherein the noise signal includes a uniform noise signal and at least one pulse signal.

15. The system according to claim 13, wherein:

the acoustic exercise includes providing at least one sequence of words while providing a time-controlled increase in noise level during the determination of the degree of hearing comprehension; and the correct resolution of the acoustic exercise includes confirmed threshold level corresponding to differentiation between two or more words or syllables in the sequence.

16. The system according to claim 12, wherein the at least one test signal comprises at least one of the following: spoken digits, numbers, sounds, syllables, phonemes, words, word groups, sentences, notes, sounds and note sequences, and melodies.

17. A non-transitory computer program product for configuration of a hearing system, wherein the computer program product, when loaded in memory and executed by at least one processor of the computer unit, causes the computer unit to carry out the following steps:

creating an acoustic test signal via a test signal generator, the acoustic test signal including at least one spoken element;

transmitting the acoustic test signal via a communication interface to the hearing system;

receiving, in a user interface, a response of a user of the hearing system, the response coding hearing comprehension of the user in relation to the at least one spoken element of the test signal;

determining a degree of hearing comprehension for the received response by comparing the received response to a corresponding reference response, the reference response corresponding to a correct resolution of an acoustic exercise represented by the test signal;

determining a modified programming for the hearing system as a function of the determined degree of hearing comprehension; and transmitting the modified programming for the hearing system using the communications interface.

18. The computer program product according to claim 17, wherein the acoustic test signal includes a noise signal and the computer unit is additionally prompted to carry out the following step:

generating an additional acoustic test signal, a noise level of the noise signal being adjusted as a function of the received response relative to a predefined signal.

19. The computer program product according to claim 18, wherein the acoustic test signal includes a distorted test signal, the distorted test signal including a predefined signal and a noise signal.

20. The computer program product according to claim 17, by which the computer unit is additionally prompted to carry out the following step:

storing the modified programming in a trainable configuration memory.

* * * * *